United States Patent [19]

Corbett, III et al.

[11] Patent Number: 5,515,848

[45] Date of Patent: May 14, 1996

[54] IMPLANTABLE MICROELECTRODE

[75] Inventors: Scott S. Corbett, III; Jerry Martyniuk, both of Portland, Oreg.; Gerald E. Loeb, Kingston, Canada; Klaus Mewes, Lilburn, Ga.; W. Eugene Skiens, Wilsonville, Oreg.; John J. Stobie, Portland, Oreg.; Doris A. Beck, Beaverton, Oreg.

[73] Assignee: PI Medical Corporation, Portland, Oreg.

[21] Appl. No.: 482,189

[22] Filed: Jun. 7, 1995

Related U.S. Application Data

[63] Continuation of Ser. No. 136,650, Oct. 14, 1993, abandoned, which is a continuation-in-part of Ser. No. 46,658, Apr. 12, 1993, abandoned, which is a division of Ser. No. 781,494, Oct. 22, 1991, Pat. No. 5,201,903.

[51] Int. Cl.$^6$ .................................................. A61B 5/042
[52] U.S. Cl. ......................................... 128/642; 607/116
[58] Field of Search .................................. 128/897, 899, 128/642, 673, 696; 174/120 R, 120 SR; 607/116–138, 154, 156

[56] References Cited

U.S. PATENT DOCUMENTS

| 3,775,552 | 4/1973 | Schumacher | 174/113 |
|---|---|---|---|
| 3,857,996 | 3/1974 | Hansen et al. | 174/113 |
| 3,881,246 | 11/1975 | Folk | 29/628 |
| 4,261,372 | 4/1981 | Hansen et al. | 128/420.6 |

(List continued on next page.)

FOREIGN PATENT DOCUMENTS

| 1115352 | 1/1981 | Canada | 128/784 |
|---|---|---|---|
| 1075562 | 3/1953 | France . | |
| 2162472 | 12/1972 | France . | |
| 654392 | 6/1951 | United Kingdom . | |
| 2233596 | 1/1991 | United Kingdom | 264/272.14 |

OTHER PUBLICATIONS

Klomp et al "Fabrication of Large Arrays of Cortical Electrodes for Use in Man" J. Biomed. Mater. Res., pp. 347–364, 1977.

The Parylene Press, No. 17, Summer 1994.

Gerald E. Loeb, M.D., Progress Toward a Visual Prosthesis, Sep. 1991, pp. 1–11.

Gerald E. Loeb, M.D., Neural prosthetic interfaces with the nervous system, May 1989, Trends in Neuroscience, vol. 12, No. 5, pp. 195–201.

(List continued on next page.)

*Primary Examiner*—William E. Kamm
*Attorney, Agent, or Firm*—Chernoff, Vilhauer, McClung & Stenzel

[57] ABSTRACT

A miniature, electrically-insulated multi-conductor electrical cable suitable for implantation in living bodies and readily connected to sensors or electrodes, and implantable microelectrodes attached to such cables. Individual electrical conductors are coated with at least one layer of, insulating material and stranded together, or optionally bound together by an additional layer of insulating material which is compatible with implantation in living bodies. The individual conductors are separated from one another in terminal portions of the cable and are held by a ribbonizing resin at a predetermined pitch to facilitate connection of each of the conductors. The terminal portions may define microelectrodes. Another microelectrode includes an electrically conductive electrode core member sharpened and coated with a thin layer of a dielectric material. An extremely small area of the core at the sharpened point is exposed by ablating the dielectric material by the use of an ultraviolet laser beam scanned over the material. Multiple conductor microelectrodes may also be supported within a hollow needle or in flat ribbon configuration, with openings in dielectric material defining active electrode sites. Multiple active electrode sites may be defined on a microelectrode accompanied by an integrated circuit after connection of the integrated circuit to a multiconductor cable.

39 Claims, 7 Drawing Sheets

U.S. PATENT DOCUMENTS

| | | | |
|---|---|---|---|
| 4,284,841 | 2/1981 | Tijunelis et al. | 174/117 |
| 4,495,917 | 3/1985 | Byers | 128/784 |
| 4,503,124 | 3/1985 | Keane et al. | 174/120 |
| 4,532,930 | 2/1985 | Crosby et al. | 128/421 |
| 4,614,028 | 3/1986 | Rich | 29/749 |
| 4,640,983 | 1/1987 | Comte | 174/119 |
| 4,800,236 | 1/1989 | Lemke | 174/113 |
| 4,804,337 | 2/1989 | Sebastien et al. | 439/449 |
| 4,809,712 | 3/1989 | Kuzma | 128/420.6 |
| 4,819,329 | 2/1989 | Haley et al. | 29/860 |
| 4,840,186 | 2/1989 | Lekholm et al. | 128/784 |
| 4,964,414 | 10/1990 | Handa et al. | 607/116 |
| 5,015,800 | 3/1991 | Vaupotic et al. | 174/34 |
| 5,074,947 | 12/1991 | Estes et al. | 156/307 |
| 5,111,812 | 2/1992 | Swanson et al. | 128/784 |
| 5,123,422 | 4/1992 | Charvin | 128/420.6 |
| 5,220,130 | 3/1993 | Walters | 174/113 |

OTHER PUBLICATIONS

Hugh S. Lusted, In Vivo Electrical Stimulation Using Multichannel Photolighographic Electrode Arrays, Aug. 1986, IEEE Transactions on Biomedical Engineering, vol. BME–33, No. 8, pp. 800–803.

Promotional Material, Repair and Recoating of Parylene Coated Printed Circuit Boards, Specialty Coating Systems, Union Carbide, 1992, p. 10.

MWS Wire Industries Technical Data Sheet—Aug. 1990, pp. 12–15.

M. J. Mela, Microperforation with Laser Beam in the Preparation of Microelectrodes, 1965, IEEE Transactions on Biomedical Engineering, vol. BME–13, No. 2, pp. 70–76.

Gerald E. Loeb, et al., Parylene as a Chronically Stable, Reproducible Microelectrode Insulator, 1977, IEEE Transactions on Biomedical Engineering, vol. BME–24, No. 2, pp. 121–128.

S. J. Tanghe, et al., A Planar IrO Multichannel Stimulating Electrode for Use in Neural Prostheses, 1990, pp. 464–467.

K. Najafi, et al., A High–Yield IC–Compatible Multichannel Recording Array, 1985, IEEE Transactions on Electron Devices, vol. ED–32, No. 7, pp. 1206–1211.

B. P. Levy, et al., Definition of the Geometric Area of a Microelectrode Tip by Plasma Etching of Paylene, 1986, IEEE Transactions on Biomedical Engineering, vol. BME–33, No. 11, pp. 1046–1049.

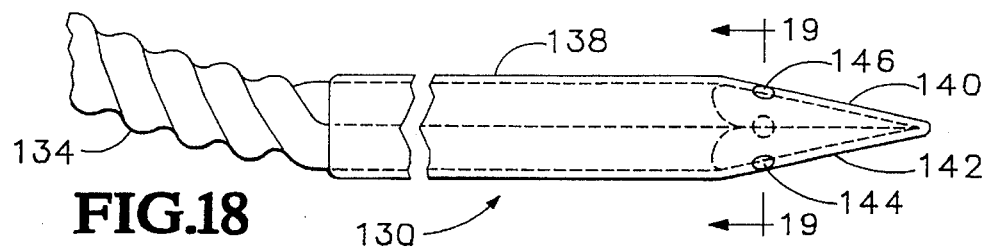
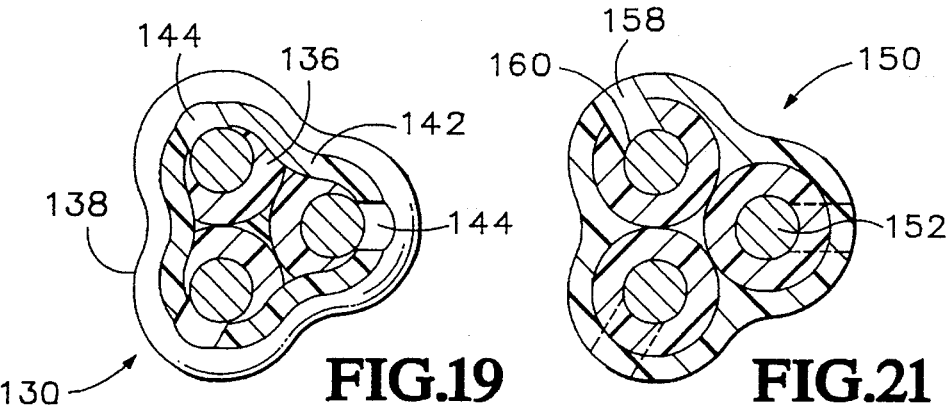
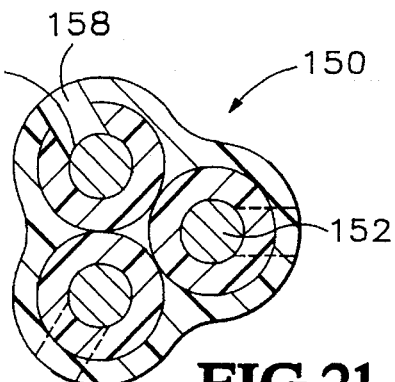
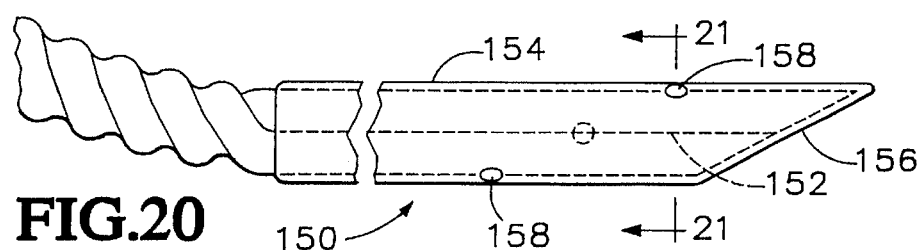
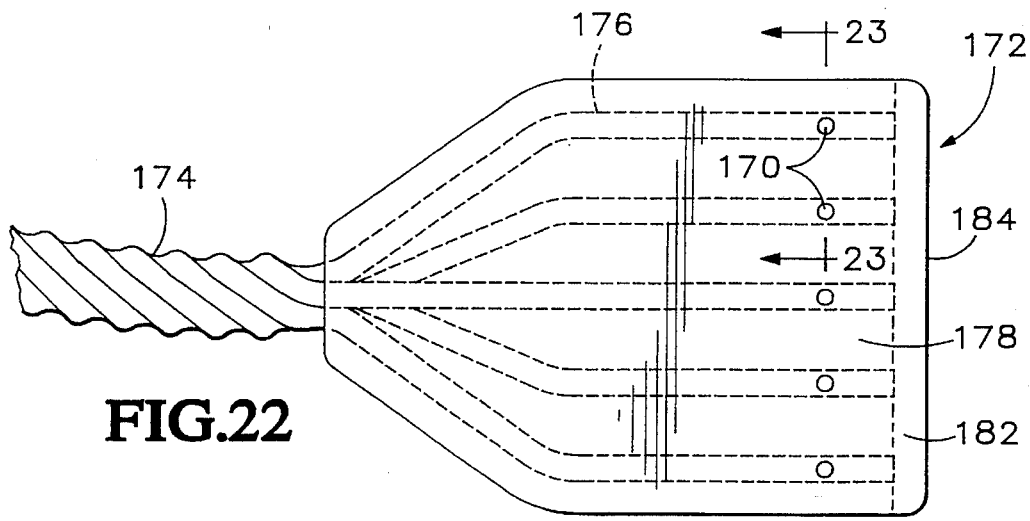
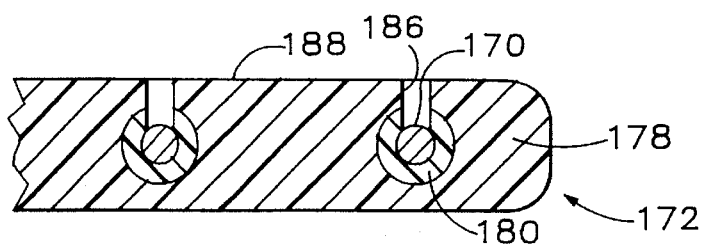

IMPLANTABLE MICROELECTRODE

This invention was made with government support under Department of Health and Human Services Small Business Innovation Research Contract #N43-NS-0-2391-00, awarded by the National Institute of Neurological Disorders and Stroke, a division of the National Institutes of Health, Department of Health and Human Services. The government has certain rights in the invention.

This is a continuation of applications Ser. No. 08/136,650, filed Oct. 14, 1993, abandoned, which is a continuation-in-part of Ser. No. 08/046,658, filed Apr. 12, 1993, abandoned, which is a division of Ser. No. 07/781,494, filed Oct. 22, 1991, now U.S. Pat. No. 5,201,903.

BACKGROUND OF THE INVENTION

The present invention relates to microelectrodes for placement within living beings to stimulate neurons electrically and to detect electrical neural activity, and relates particularly to the definition of electrode contact surfaces for such electrodes.

For several years research has been conducted in attempts to establish communication through living neurons, to communicate to the human brain information which can no longer be provided by a person's own eyes or ears, to stimulate paralyzed muscles, to stimulate autonomic nerves, as to control bladder function or pace the heart, or to control prosthetic limbs.

It is well known that electrical stimulation of certain nerves and certain regions of the brain can be perceived consciously, and research is being performed with the intention of eventually learning how to stimulate nerves in ways which can provide useful information to a person whose ability to hear or to see has been lost.

To utilize neural prostheses, electrical connections must be made to living neurons. Such connections must be made by extremely small electrodes, in order to isolate currents within small regions of living tissue. Active electrode sites can be placed very close to nerve cells, and electrical activity at the active electrode sites can be used to provide stimulation to the nerves. To limit the mechanical trauma caused by insertion and chronic presence of electrode structures, the entire electrode structure and associated wires must be as small as possible consistent with the required ability to conduct electrical energy, and must be of materials which will not react with the living body.

Implanted electrodes and conductors connected to them must be electrically insulated very effectively, because of the very small voltages and currents being utilized. The localized nature of the electrical potential gradient which must be detected by a microelectrode, and the fragility of neurons, dictate a microelectrode tip with small dimensions (typically less than 5×25 microns), which in turn produces a high impedance in the interface of metal to electrolyte. Since the probe as a whole must have a slender profile to minimize disruption of tissue, the requirement to minimize shunt losses along the insulated shank of the probe falls on a very thin dielectric coating which must be cleanly excluded from the tiny exposed tip or window. Insulating coatings on conductors must be free from pinholes and should be tightly adhered to the insulated wires and parts of electrodes. It is known that there are some biologically compatible dielectric materials which can be applied consistently and successfully as coatings of uniform thickness for such small structures as are found in microelectrodes to be used for neural prostheses. An insulating coating of Parylene-C®, a polymerized diparachloroxylyene produced by the Union Carbide Corporation, is known to have the required biological compatibility and electrical insulation qualities and can be applied successfully to electrode surfaces, but the techniques previously available for removing portions of such a coating have not been entirely satisfactory.

At the same time, active contact sites of the electrodes must be clean and must typically present as low a resistance as is possible to electrical current at their surfaces. Although current is necessarily very small, because of the need to carry current pulses to very small regions, current density is significant in the small, exposed active contact site surface of an electrode, where it is exposed to the saline environment within a living body, and the electrode must be of a corrosion-resistant material to avoid electrochemical damage to the exposed surface of the electrode or the adjacent tissue through ion migration or other mechanisms.

Microelectrode tips require well defined active electrode sites for use as stimulation electrodes. A limiting factor in producing microelectrodes to be used in stimulating and receiving information from neurons is the ability to remove small areas of insulation cleanly and accurately, leaving clean electrode contact surfaces of limited size to be exposed to neurons. Various techniques for exposing portions of an electrode have been used in the past, but it is difficult to accurately reproduce the desired tip exposure using them. Such techniques have included AC electric corona arcing, direct heating, and plasma etching. These methods have not been completely satisfactory, either because they fail to leave a cleanly and accurately exposed electrode surface, or because the remaining adjacent insulating coating does not adhere satisfactorily and tightly to the microelectrode adjacent the exposed surfaces. Mechanical removal of an insulating coating has been very time-consuming and has a high probability of damaging the tip.

Multiple conductor microelectrodes have been produced using photolithographic integrated circuit production techniques, but these are not robust enough for some applications, and are very expensive to produce in small numbers. Since they are produced as small integrated circuits they lack conductors for connection to other electrical circuitry. It is difficult to attach conductors to such devices and then protect surfaces in the vicinity of such connections to prevent undesired electrical activity when implanted.

Use of lasers to pierce dielectric coatings in preparation of microelectrodes was described by M. J. Mela in 1965 in an article entitled "Microperforation with Laser Beam in the Preparation of Microelectrodes," published in IEEE Transactions on Biomedical Engineering, Vol. BME-13, No. 2, pp. 70–76. Mela disclosed use of a red light ruby laser, which does not satisfactorily clean insulating coatings from metal surfaces, as is needed for suitably low surface resistance. That is, before the present invention it has not been known how to remove biologically compatible dielectric materials cleanly from a metal surface using a laser to produce well-defined surface areas for contact in order to achieve a well-defined surface resistance.

What is still needed, then, is a microelectrode and a method for manufacturing such a microelectrode which is suitable for chronic biological implantation, which defines contact surfaces cleanly exposed, of an accurately predetermined and controlled size and location, and surrounded by effectively and securely attached dielectric material.

SUMMARY OF THE INVENTION

The present invention provides improved microelectrodes and a method for manufacturing such microelectrodes suitable for chronic implantation in a living person to accomplish electrical stimulation of nerves and to sense electrical activity within nerves.

In accordance with the present invention a miniature multi-conductor electrical cable is provided in which each of a plurality of fine wires of a suitably flexible material such as gold or a platinum-iridium alloy is coated with an insulating material. For example, a thin layer of a resin such as a polyimide covered by a second coating of a polyester-imide insulating material is very effective as an insulating dielectric system, without greatly increasing the force required to bend the cable. Alternatively, a single layer of a polymeric resin such as a polytetrafluoroethylene material (PTFE), perfluorinated ethylenepropylene copolymer (FEP), perfluorinated ethylene-vinyl alkoxy ether copolymer (PFA), silicone, or polyurethane may be used as an insulating coating for individual conductors.

The coated wires of the cable according to the present invention are held together, either by being stranded together, as in a seven-conductor helical stranding, or by an additional coating of an insulating material at least partially surrounding each conductor and interconnecting each conductor with an adjacent conductor along at least an intermediate portion of the length of the conductors. The conductors may be held together by such an additional coating either as a ribbon-like arrangement of parallel conductors, or in a circular configuration as either a solid-core strand or a hollow strand defining a central lumen between the interconnected helically arranged conductors.

A cable which is one embodiment of the present invention includes an intermediate portion of the cable including several closely adjacent electrical conductors and a ribbonized terminal portion adjacent at least one end of the cable, including a transition portion in which the conductors diverge from one another and merge into a terminal portion in which the several conductors are held at a predetermined spacing, or pitch, with respect to each other. In the terminal portion the conductors are preferably encapsulated and thus held in a ribbonized form, but with a respective small length of each of the conductors exposed, free of insulating material, as an electrically connectable portion of the cable.

In accordance with the present invention a biologically implantable multiconductor microelectrode comprises a plurality of fine wires electrically insulated from each other and held together in a predetermined spatial relationship with each other by a quantity of a dielectric material through which an opening is defined to expose a predetermined area of each of such fine wires through a respective one of the openings. In some embodiments of the invention, conductive metal may be deposited and electrically connected with the surface of the respective one of the fine wires in each of the openings, presenting an exterior surface of corrosion-resistant metal having a desired conductivity.

In one embodiment of the microelectrode according to the invention several fine wires are wrapped about a support core which may be a wire or a small tube.

In another embodiment of the microelectrode of the invention, several fine wires are arranged in a generally planar array, parallel with each other, and active electrode sites are defined by openings through the dielectric material, exposing cleanly a surface of a respective wire at a respective location in the planar array.

In yet another embodiment of the invention a microelectrode assembly incorporates active electrode sites located on a substrate chip of an integrated circuit. A cable of fine wire conductors is connected to terminal pads on the substrate and leads away from the microelectrode. The entire microelectrode assembly has a coating of a biologically implantable dielectric material, and active electrode sites are located in openings cut through the coating of dielectric material by the use of a beam of ultraviolet light, as from a laser, to expose conductive material located there on the substrate.

According to the method of the invention, a biologically implantable microelectrode is prepared by directing a highly focused beam of ultraviolet light of sufficient intensity, such as a laser beam, onto a coating of dielectric material on a conductor body of an electrode, to ablate dielectric material to define an active electrode site on a portion of the electrode conductor body. In one method according to the present invention, the ultraviolet light is provided by a laser beam and is also used to briefly thermally fuse a quantity of the dielectric material located immediately adjacent the active electrode site, allowing the dielectric material to resolidify adhered to the electrode conductor body.

In a further method according to the present invention a plurality of fine wires are held together in a predetermined spatial relationship to each other by a biologically implantable dielectric material, and active electrode sites are prepared by directing a beam of ultraviolet light, as from a laser, onto predetermined locations in a distal end portion of the multiconductor microelectrode. The fine wires held together and stiffened by coatings of dielectric material to form the implantable microelectrode extend away from the microelectrode in the form of a flexible group or cable of fine wires to be connected to other electrical circuitry.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 18 is a view of a biologically implantable multiconductor microelectrode which is yet a further embodiment of the present invention, together with a portion of a multiconductor cable connected thereto.

FIG. 19 is a sectional view, taken along line 19—19 of FIG. 18, at an enlarged scale.

FIG. 20 is a view of a biologically implantable multiconductor microelectrode which is yet a further embodiment of the present invention, together with a portion of a multiconductor cable connected thereto.

FIG. 21 is a sectional view, taken along line 21—21 of FIG. 20, at an enlarged scale.

FIG. 22 is a plan view of a biologically implantable multiconductor microelectrode which is yet a further embodiment of the present invention.

FIG. 23 is a sectional view of a detail of the microelectrode shown in FIG. 22, taken along line 23—23 at an enlarged scale.

DETAILED DESCRIPTION OF THE INVENTION

Figure 1:
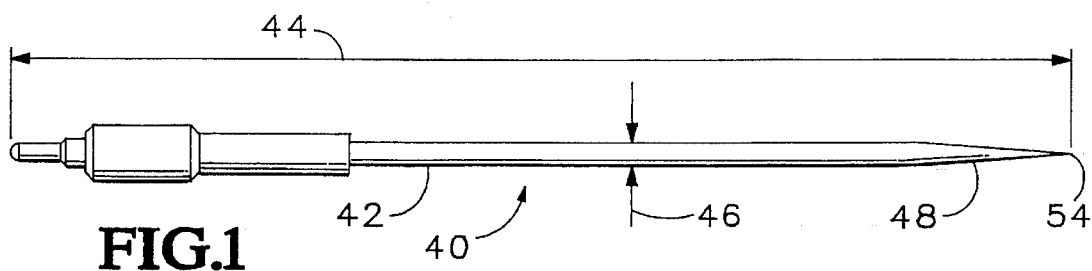
FIG. 1 is a view of a biologically implantable, single-conductor microelectrode including an active electrode site prepared according to the present invention.
Figure 2:
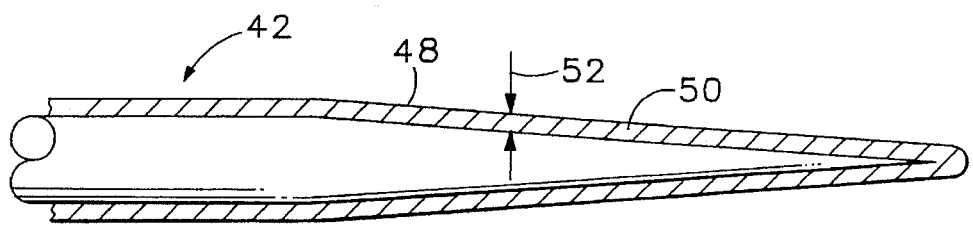
FIG. 2 is a detail view, at an enlarged scale, of the distal end of the microelectrode shown in FIG. 1 during the process of preparation of an active electrode site.
Figure 3:
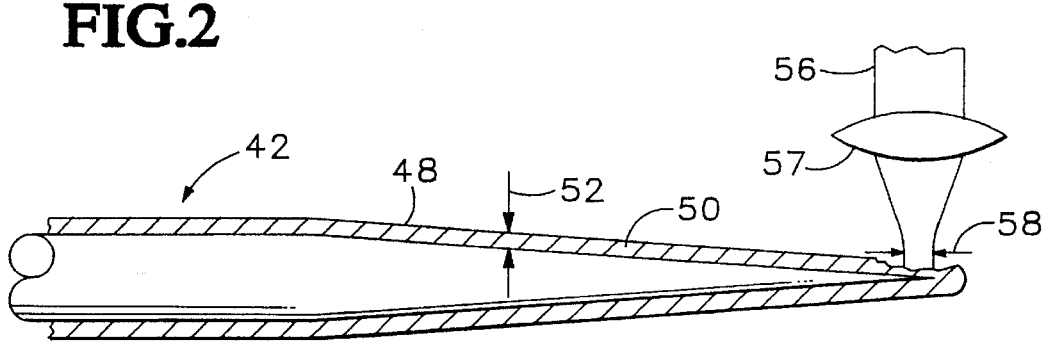
FIG. 3 is a view similar to FIG. 2, showing a further stage in the process of preparation of an active electrode site.

Referring now to the drawings which form a part of the disclosure, and particularly referring to FIGS. 1-4, a microelectrode 40 having a conductor body 42 generally in the form of a straight needle of a platinum-iridium alloy or other suitable metal with a conically pointed tip, and may have a length of, for example, three inches and a diameter 46 of 0.010 inch (250 µm). The conductor body 42 has a conical distal end 48 and the body 42 including the distal end 48 is covered with a thin film coating of a dielectric material 50 which is compatible with being implanted within a living body. Dielectric materials which are useable for such a coating include fluorocarbons, polyimides or derivatives thereof, epoxies, enamel, or a polymer of para-chloroxylylene, such as that available from Union Carbide Corporation under the trademark Parylene-C®. Such dielectric materials are provided in the form of very thin film coatings, applied so as to completely cover the surfaces of the microelectrode. Such a film of dielectric material 50 has, for example, a thickness 52 of 6–12 µm of Parylene-C® vacuum deposited on the surface of the electrode conductor body 42.

An active electrode site 54 is provided at the distal end 48 of the microelectrode by ablating the coating of dielectric material 50 by exposing it to a scanned highly-focused ultraviolet laser beam 56. Preferably, for use of the electrode in providing electrical interconnection with neurons, an active electrode site about 0.001 inch (25 microns) long including the sharpened point of the electrode body is cleaned of its dielectric coating by use of such a laser beam 56, focused to a spot having a diameter 58 on the order of 25 µm.

For example, a frequency-quadrupled YAG (FQY) laser operated in the fundamental transverse electromagnetic (TEM$_{00}$) mode is suitable to ablate portions of the coating 50. Typically, this laser is Q-switched at around 1–20 KHz, producing a 40 ns full-width half maximum (FWHM) pulse which is focused by a focusing lens 57 to about a 25 µm spot, producing a fluence of approximately 1–5 joules/cm$^2$ at an average power of 10–50 milliwatts. Such a laser has a 266 nanometer wavelength which is in the ultraviolet (UV) range.

It has been found that such a highly focused laser beam in the ultraviolet frequency band is readily absorbed by the dielectric coating materials mentioned above, and that it is also absorbed by the surfaces of metals such as platinum or iridium, used as the conductor body 42 of such an electrode 40, with the result that the dielectric materials are both vaporized and photoablated, removing them cleanly from the surfaces of the metal of the electrode body 42. The mechanism by which this ablation of the dielectric material occurs is not definitely known, but it is believed to be a combination of conversion of the laser light energy to heat in the dielectric material 50 and the underlying metal, which acts primarily by evaporating the dielectric material without leaving an ash, and by some chemical dissociation of the polymeric dielectric material induced by the UV light energy. Additionally, the underlying surfaces of the metal of the electrode conductor body 42 are heated very quickly to temperatures apparently exceeding 1000° C., which vaporizes remaining polymeric dielectric material, leaving the surface of the metal clean as a relatively low resistance contact surface for a conduction of electrical current.

The FQY laser beam spot can be moved under computer software control to scan the dielectric material to remove it from the conductor body. Scanning control can be provided, for example, by equipment designed to control lasers for use in manufacture of integrated circuit products, such as is available from Electro Scientific Industries, Inc., of Beaverton, Oreg. Preferably, the UV laser is utilized together with exhaust and positive gas pressure systems to keep debris away from the focusing lens and the area where dielectric material is being ablated. Operation of the laser at the powers mentioned above provides an effective range of etch depths of approximately 1–50 microns in polyimide or Parylene-C® (polypara-chloroxylylene).

Surfaces of the dielectric material 50 remaining adjacent the active electrode site are also heated by the effects of the UV laser beam, fusing the dielectric material briefly. The dielectric material 50 resolidifies adhering tightly to the surface 60 of the metal of the conductor body of the electrode, and with a smooth exterior surface 62 exposed.

Figure 4:
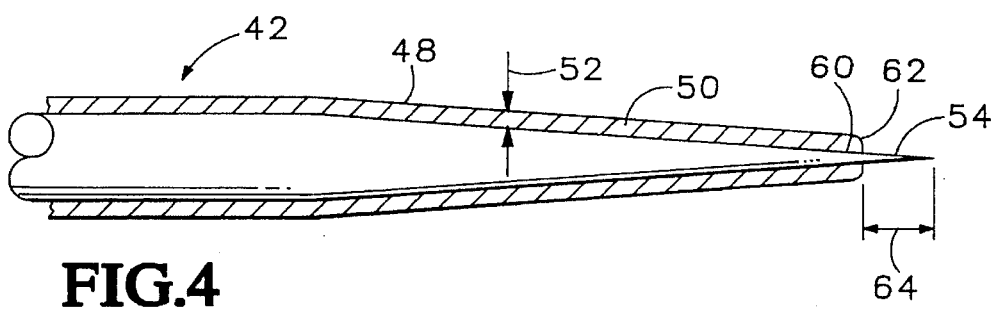
FIG. 4 is a view similar to FIG. 2, showing the completed active electrode site.
Figure 5:
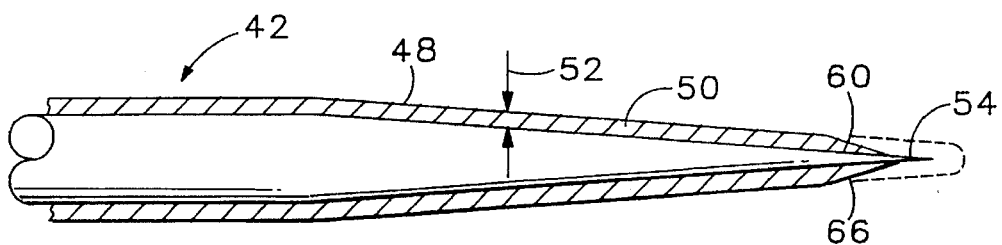
FIG. 5 is a view similar to FIG. 4, showing a detail of a microelectrode prepared according to the present invention with a somewhat different active electrode site.
Figure 6:
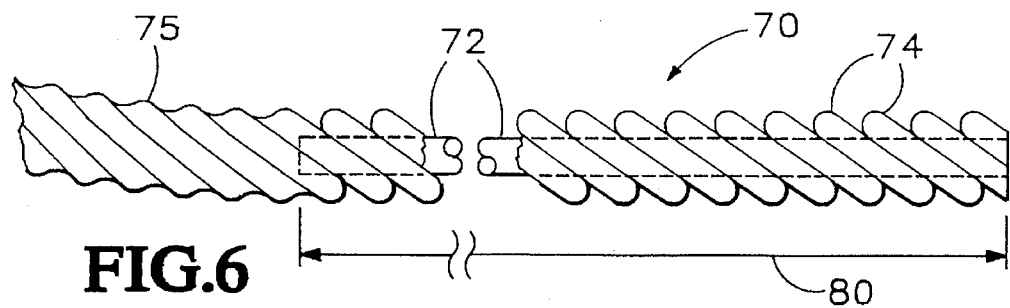
FIG. 6 is a view of a biologically implantable microelectrode multiconductor according to the present invention, at an early stage of preparation, together with a portion of a stranded cable connected to the microelectrode.

As shown in FIG. 4, the dielectric material 50 may be cut sharply away leaving a full-thickness layer of dielectric material 50 adjacent the active electrode site, while as shown in FIG. 5, the remaining dielectric material 50 is tapered in the area 66 adjacent the active electrode site 54, by selectively etching to different, shallower, depths, proceeding away from the active electrode site 54, thus sculpting the microelectrode in a manner to reduce insertion trauma. Using the method of the invention, an active electrode site 54 can be prepared with an exposed sharp point having a length 64 as small as 25 μm.

A biologically implantable multiconductor microelectrode 70, shown in FIGS. 6–13, includes a core 72, which may be of solid metal similar to that used for the conductor body 42 of the implantable electrode 40 described previously, or may be of tungsten. Several extremely fine wires 74, for example, six platinum-iridium alloy wires of American Wire Gauge 52, having a wire diameter of approximately 18 μm (0.0007 inch), extend from a helically stranded multiconductor cable 75 of such wires each insulated and connected to each other by suitable coatings of flexible dielectric material (shown in the drawings with greatly exaggerated thickness for the sake of clarity). The fine wires 74 are wrapped around the solid core 72 in a helical serving in which the individual fine wires 74 lie neatly alongside one another without overlapping. Each of the wires 74 has an individual thin coating 76 (FIG. 9) of dielectric material, preferably polypara-chloroxylylene (Parylene-C®), and a further coating 78 of Parylene-C® or other dielectric material adhesively attaches the fine wires 74 to one another and to the core 72, forming a monolithic, elongate multiconductor microelectrode body having a desired length 80 of, for example, 3 cm.

Figure 7:
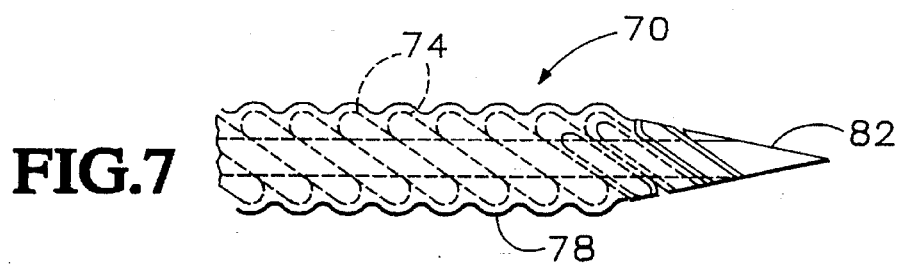
FIG. 7 is a detail view of the distal end of the microelectrode shown in FIG. 6, at a later stage of preparation.

The fine wires 74 and the core 72 are neatly cut and tapered to form a sharp conical point 82 at the end of the microelectrode 70, as shown in FIG. 7, for example, by precise abrasion, using lapidary techniques, and/or other methods including chemical etching, selective heating, laser ablation, or electrophoresis. After the distal end of the microelectrode 70 has been shaped, an additional thin coating 84 of dielectric material is added, at least over the portions of the microelectrode which have been affected by the process of forming the sharp conical point 82, again providing an insulating and completely tight coating.

Using the UV laser beam as previously described, an active electrode site 86 is provided on each of the fine wires 74 by ablating the dielectric material of the coatings 76, 78 and 84 from the wire over an area of about 250 square microns, for example, forming a circular opening 88 about 18 μm (0.0007 inches) in diameter through the dielectric material covering each of the fine wires 74. As described previously in connection with the single microelectrode 40, a shallow surface layer of the dielectric material surrounding the cleaned metal surface forming each of the active electrode sites is fused and resolidified in close adhesion to the metal surface of the fine wire, as may be seen in FIG. 9.

Figure 8:
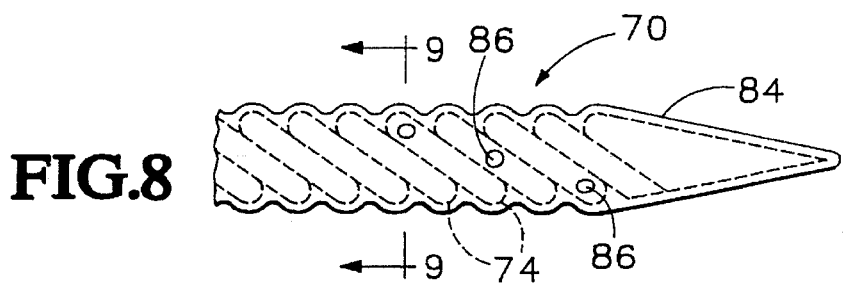
FIG. 8 is a view similar to that of FIG. 7 showing the completed microelectrode.
Figure 9:
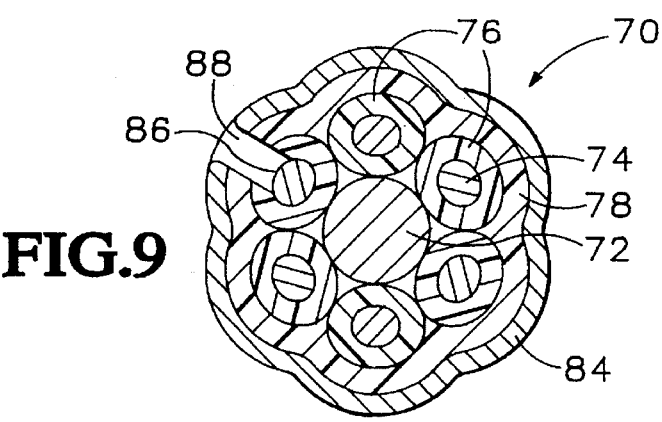
FIG. 9 is a section view taken along line 9—9 of FIG. 8.
Figure 10:
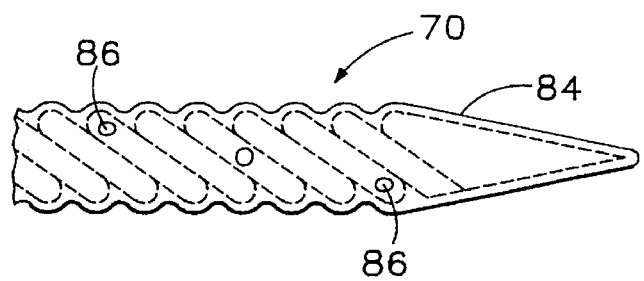
FIG. 10 is a view similar to that of FIG. 8, showing a microelectrode which is a slightly different embodiment of the invention.

The spacing and orientation of the active electrode sites 86 corresponding to the several fine wires 74 may be chosen as desired consistent with the pitch of the helical wrapping of the fine wires about the core. When desired, the active electrode sites 86 may be spaced radially about the multiconductor microelectrode 70, or, as shown in FIGS. 8 and 10, they may be spaced longitudinally in a helical arrangement along the microelectrode 70, separated more or less from one another as determined by the number of adjacent ones of the fine wires 74 which are skipped between consecutive active contact sites 86 defined along the microelectrode 70.

Figure 11:
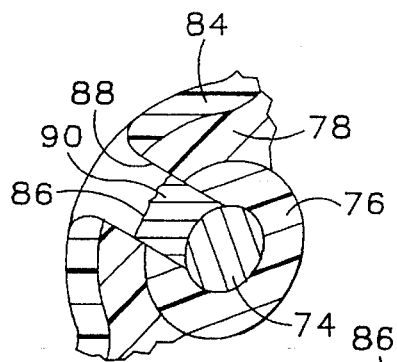
FIG. 11 is a view of a portion of FIG. 9, at a further enlarged scale, showing an active electrode site including a deposit of conductive material within an opening through a coating of dielectric material.
Figure 12:
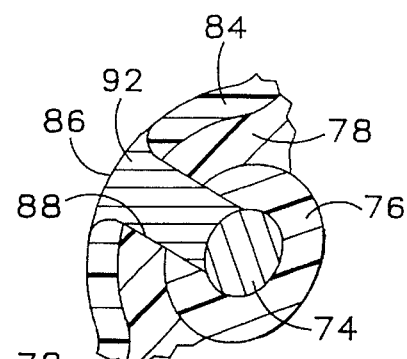
FIG. 12 is a view similar to FIG. 11, showing an active electrode site including a deposit of conductive material flush with an outer surface of a dielectric material surrounding a conductor.
Figure 13:
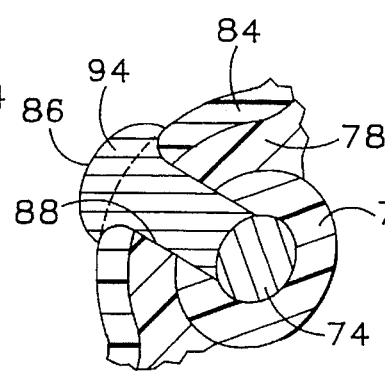
FIG. 13 is a view similar to FIG. 11, showing an active electrode site including a deposit of conductive material protruding beyond an outer surface of surrounding dielectric material.
Figure 14:
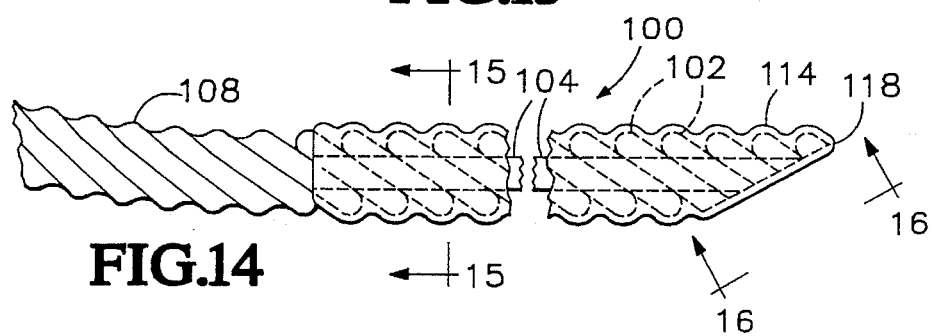
FIG. 14 is a view of a biologically implantable multiconductor microelectrode which is another embodiment of the invention, together with a portion of a multiconductor cable connected thereto.
Figure 15:
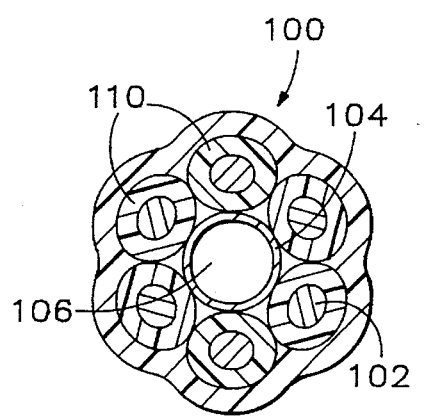
FIG. 15 is a sectional view taken along line 15—15 of FIG. 14, at an enlarged scale.
Figure 16:
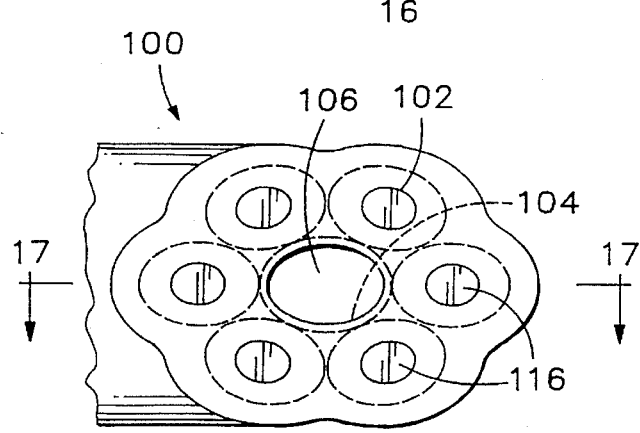
FIG. 16 is a view of a beveled end surface of the microelectrode shown in FIG. 14, taken in the direction indicated by the line 16—16.
Figure 17:
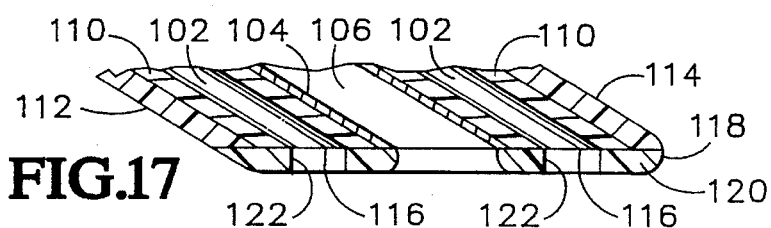
FIG. 17 is a sectional view of a detail of the microelectrode shown in FIG. 14, taken along the line 17—17 of FIG. 16.

Depending upon the intended use of the microelectrode, the openings 88 of the active electrode sites 86 may be left as depressions relative to the outer surface of the outer coating 84 or 78 of dielectric material, or suitable deposits of metal having desired conductivity and resistance to electrochemical corrosion-resistant may be provided electrophoretic deposition, with such deposits attached to and electrically interconnected to the cleaned surface of the fine wire 74, either partly filling the openings 88 defined through the dielectric material, as with the deposit 90 shown in FIG. 11, filling the opening flush with the outer surface of the dielectric material, as with the deposit 92 shown in FIG. 12, or forming a small bump standing proud above the outer surface of the dielectric material, as with the deposit 94 shown in FIG. 13.

Where a core 72 of wire is not desired a quantity of the dielectric material may be deposited at the distal end of the multiconductor microelectrode and shaped to the desired tip configuration.

The several fine wires continue away from the electrode, and may be held together as a helical strand or, depending upon the application, may be held together in a planar ribbon cable form to a desired length for connection through use of connectors (not shown) to electric equipment associated with use of the microelectrode 70 described herein.

A biologically implantable multiconductor microelectrode 100 somewhat similar to the microelectrode 70 is shown in FIGS. 14–17 and also has a plurality of conductors such as fine wires 102 formed into a helical serving, about either a solid core (not shown) or a thin-walled tube 104 to define a lumen 106 within the microelectrode 100. The fine wires 102 are extensions of the conductors of a slender multiconductor cable 108 similar to the cable 75 described previously. The individual fine wires 102 have respective coatings 110 of a biologically implantable dielectric material, and have been overcoated by a coating 112 of similar dielectric material to hold them together in the desired helical form attached to the tube 104. The distal end 114 of the microelectrode is cut along a plane extending obliquely with respect to the central longitudinal axis 116 of the electrode to form a beveled point 118, as by the use of lapidary techniques with the microelectrode held potted in a body of material which can later be removed. For example the electrode may be potted or held firmly attached to a substrate, such as a glass slide, to stiffen it and facilitate the cutting process. The material holding the microelectrode to the substrate could be Aremco Crystal Bond 509, a thermoplastic microcrystalline wax-based adhesive available from Aremco Products, Inc. of Ossining, N.Y. This material may later be removed by solution in acetone, which does not dissolve the Parylene-C® dielectric material, with optional application of heat to make the process more rapid. After the beveled point 118 is formed, an additional layer 120 of similar dielectric material is applied to the distal end 114 of the multiconductor microelectrode. An active electrode site 116 is defined, by using a UV laser as previously described to ablate the dielectric material of the layer 120 and form openings 122 having the desired size, which may be similar to that of the active electrode sites 86 described previously, on the end of each of the fine wires 102 as they are presented on the beveled surface of the distal end 114 of the microelectrode.

The active electrode sites 116 may each, as described above in connection with the microelectrode 70, also be partly or fully filled with a deposit (not shown) of a desired metal electrophoretically deposited onto the surface of the fine wire 102 to provide partial filling of the opening 122, to fill the opening 122 flush with the outer surface of the dielectric material, or to provide a small bump standing proud above the outer surface of the dielectric material of the layer 120.

A biologically implantable multiconductor microelectrode 130, shown in FIGS. 18 and 19 includes three straight, parallel fine wires 132, which are continuations of the several conductors of a cable 134. Each of the fine wires 132 is coated individually with a layer 136 of biologically implantable dielectric material. The three fine wires 132 are held together as a group by an adhesive overcoating 138 of similar dielectric material. The dielectric material may, both for the individual coatings 136 on the fine wires 132 and for the additional material holding the coated wires 132 together, be one of the types of materials mentioned previously in connection with the electrode 40. In some cases it may also be desirable to add a further coating (not shown) of dielectric material such as an epoxy or enamel over all or part of the length of the microelectrode 130 to add mechanical stiffness to the microelectrode 130, in order to facilitate insertion through tissue surrounding a nerve.

A distal end 140 of the microelectrode 130 is sharpened into a generally conical point using lapidary techniques, after which an additional coating 142 of dielectric material is applied to at least the distal end portion of the microelectrode 130 to provide a tightly adhered impervious coating covering the entire microelectrode 130. Thereafter, openings 144 are formed by use of an ultraviolet laser beam in the manner described previously, providing three active electrode sites 146 located close together on the tapered point portion of the distal end 140 of the microelectrode 130. Use of the UV laser to form the openings 144 affords accurate control over the size of each active electrode site 146, so that a desired impedance will be provided uniformly at each active electrode site 146.

As mentioned above previously in connection with the microelectrodes 70 and 100, additional conductive material can be electrophoretically deposited in contact with the fine wires 132 to build up the active electrode sites within the openings 144 formed in the dielectric material by the UV laser, so that the available contact surface area of the active electrode sites 146 may be located slightly below, flush with, or proud above the outer surface of the dielectric material of the outer coating 142 on the distal end 140.

A multiconductor microelectrode 150 shown in FIGS. 20 and 21 is similar to the microelectrode 130 just described, in that it includes several straight fine wires 152, parallel with each other and insulated from and held parallel with each other by dielectric material. An additional external coating of dielectric material may also be utilized to provide structural support, stiffening the electrode. The distal end 156 of the microelectrode is sharpened by being cut at a bevel angle, as may be accomplished by potting the distal end 156 of the microelectrode and using lapidary techniques, to form the shape shown in FIG. 20. Thereafter a final coating 154 of dielectric material is applied and a UV laser is utilized as previously described to define openings 158 through the layers of dielectric material to provide an active electrode site 160 on each of the fine wires of the microelectrode. Such active electrode sites 160 may, as illustrated in FIG. 20, be spaced apart from one another longitudinally of the microelectrode 150, although they could all be located at the same position longitudinally of the microelectrode 150.

It will be understood that deposits of metal of appropriate conductivity and resistance to electrochemical corrosion may be electrophoretically deposited on each of the active electrode sites 160 of the microelectrode 150 as described previously with respect to other microelectrodes according to the invention.

It will also be understood that as few as two fine wires 152, or four or more fine wires 152, may be grouped together, extending parallel with one another and held together by dielectric coatings as a microelectrode 130 or 150.

For use in situations where a surface contact with a nerve is desired, a generally planar array of active electrode sites 170 of a biologically implantable multiconductor microelectrode 172, shown in FIGS. 22 and 23 according to the present invention may be provided in connection with a biologically implantable cable 174 similar to that disclosed in Corbett, III, et al. U.S. Pat. No. 5,201,903, of which the disclosure is hereby incorporated herein by reference. A helically stranded multiconductor cable 174 of fine wires 176 extends to the microelectrode 172, which has a generally planar body 178 including a quantity of dielectric material surrounding and supporting each of the wires 176, which are preferably coated individually with a layer 180 of dielectric material. The wires 176 are fanned out from one another in the planar body 178 to lie parallel with and spaced apart from one another by a desired pitch which may be a distance such as 150 μm (6 mils). A layer 182 of dielectric material is added to the distal end 184 of the microelectrode body 178 to insulate the distal end of each fine wire 176. Active electrode sites 170 are provided by forming openings 186 through the dielectric material of the body 178 and the layer 180 surrounding each fine wire 176 with the use of an ultraviolet laser as previously described to provide a clean contact surface area of a predetermined size on each of the fine wires 176. The placement of the active electrode sites 170 on the microelectrode 172 may be chosen to correspond with the requirements for use of the microelectrode.

Additional electrically conductive materials may be deposited in the openings 186, in contact with the exposed surfaces of the fine wires 176 to provide the desired location of the eventual contact surface of the active electrode sites 170 with respect to the outer surface 188 of the planar body 178 surrounding the fine wires 176.

Figure 24:
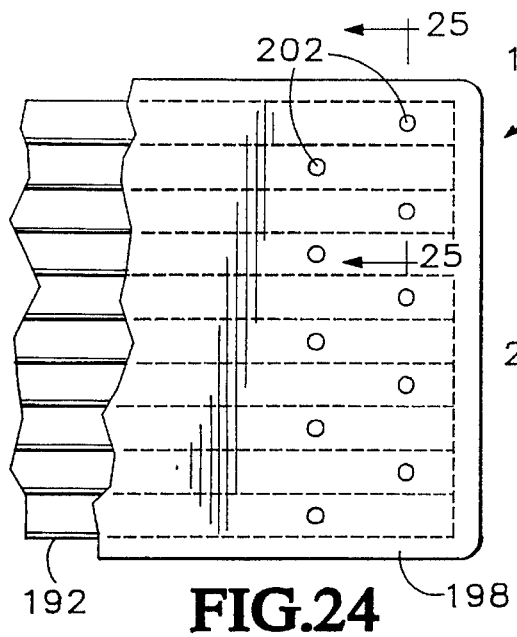
FIG. 24 is a view of a biologically implantable multiconductor microelectrode according to the present invention, embodied in a ribbon-cable.
Figure 25:
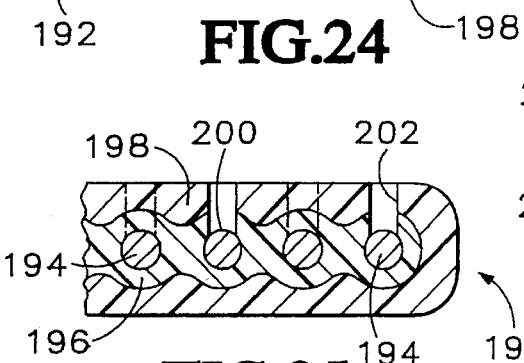
FIG. 25 is a sectional view, taken along line 25—25 at an enlarged scale, of a detail of the microelectrode shown in FIG. 24.

In yet a further alternative embodiment of the present invention, shown in FIGS. 24 and 25, a biologically implantable multiconductor microelectrode 190 according to the present invention may be formed at a distal end of a ribbon cable 192 in which several fine wires 194 are held closely together side-by-side in a ribbon-like configuration by a coating of dielectric material 196 surrounding each of the fine wires 194 and holding the several wires 194 together parallel but spaced apart slightly from each other. A further coating 198 of dielectric material is provided at the distal end of the ribbon-cable 192, and active electrode sites 200 are prepared by using a UV laser, as previously described, to provide openings 202 through the layers 196, 198 of dielectric material, exposing a predetermined small area of the surface of each of the several fine wires 194.

Figure 26:
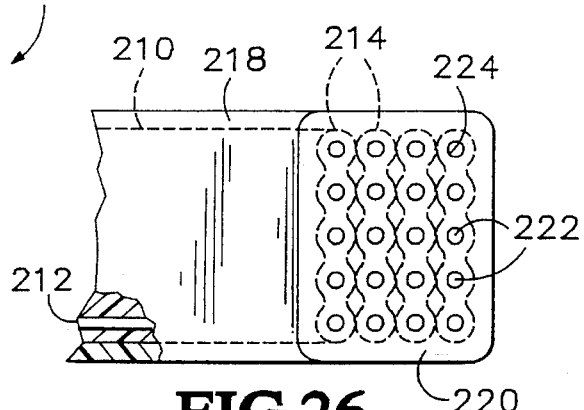
FIG. 26 is a front view of a biologically implantable multiconductor microelectrode according to the present invention, including an array of active electrode sites.
Figure 27:
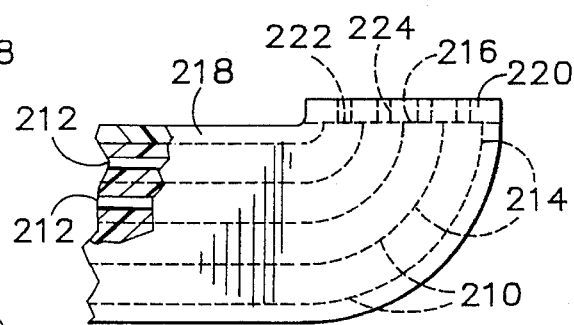
FIG. 27 is a side view of the microelectrode shown in FIG. 26.
Figure 28:
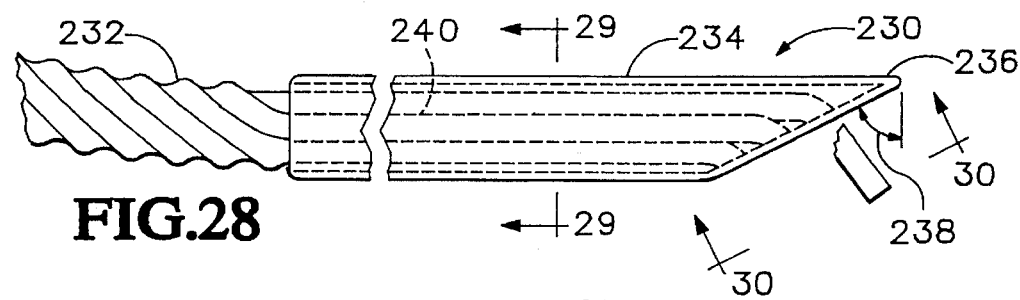
FIG. 28 is a view of a biologically implantable multiconductor microelectrode according to the present invention including a tubular needle, together with a portion of a multiconductor cable connected thereto.
Figure 29:
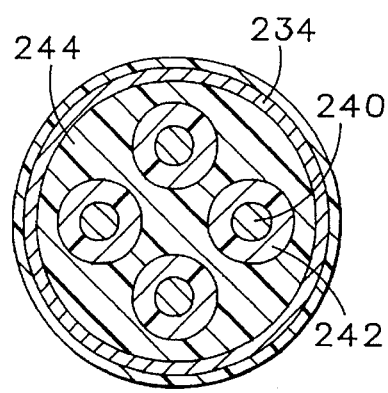
FIG. 29 is a section view, taken along line 29—29 at an enlarged scale, of the microelectrode shown in FIG. 28.

Similarly, as shown in FIGS. 26 and 27, several ribbon-cables 210 of fine wires 212 may be arranged parallel with one another, with a distal end portion 214 of each separate ribbon-cable 210 bent, so that the respective fine wires 212 extend generally normal to the length of the several ribbon-cables at a contact area face 216. The several ribbon-cables 210 are held together by a coating 218 of dielectric material, and the contact area face 216, prepared by lapidary techniques, for example, exposes a distal end of each of the fine wires 212. A final coating 220 of biologically implantable dielectric material is applied to the face 216. An active electrode site 222 for each of the fine wires 212 is prepared by using an ultraviolet laser as described previously to form a respective opening 224 extending through the coating 220 of dielectric material to expose the surface of the distal end of each fine wire 212. A deposit of additional electrically conductive metal (not shown) may be electrophoretically formed on the exposed surface of each fine wire 212 as previously described.

Figure 30:
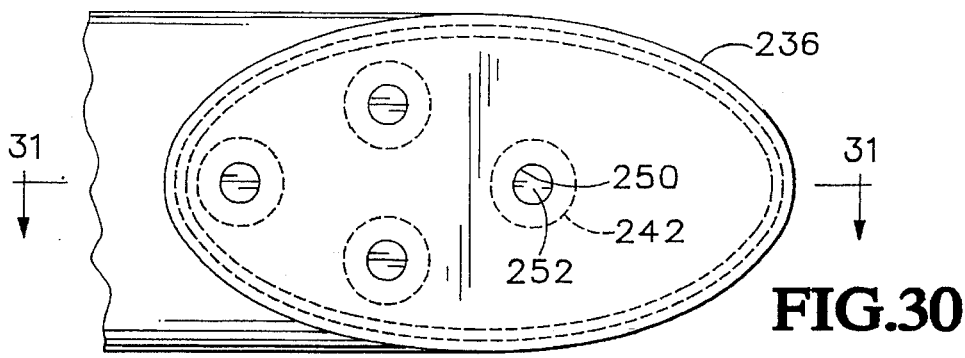
FIG. 30 is a view, taken along line 30—30 at an enlarged scale, of the distal end of the microelectrode shown in FIG. 28.
Figure 31:
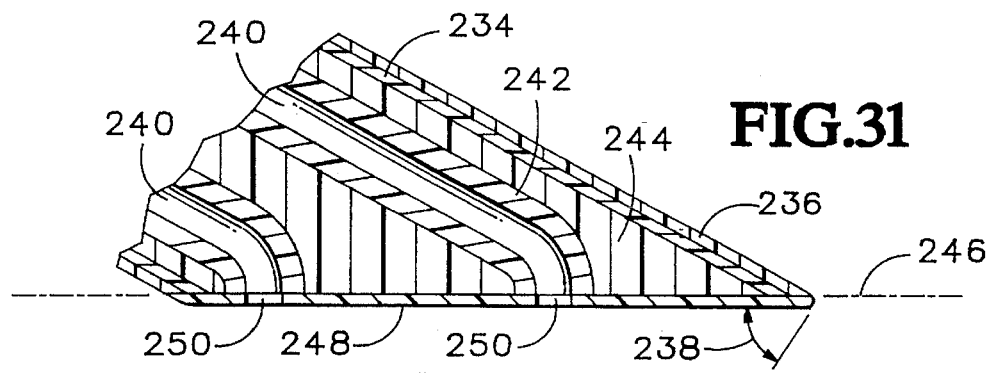
FIG. 31 is a sectional view, taken along line 31—31 of FIG. 30.
Figure 32:
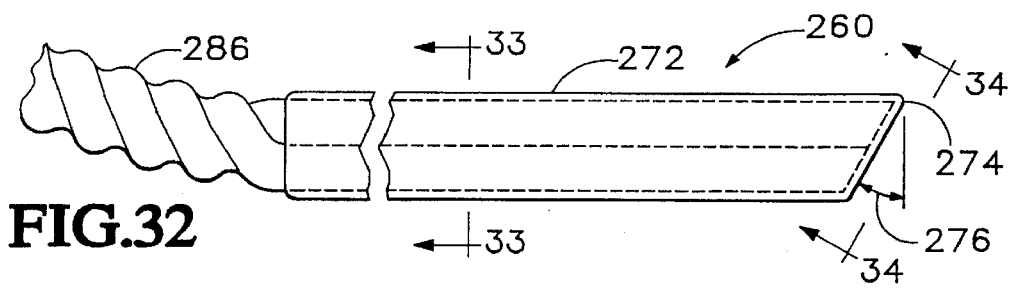
FIG. 32 is a view of a biologically implantable multiconductor microelectrode according to the present invention including bipolar active electrode sites.
Figures 33, 34:
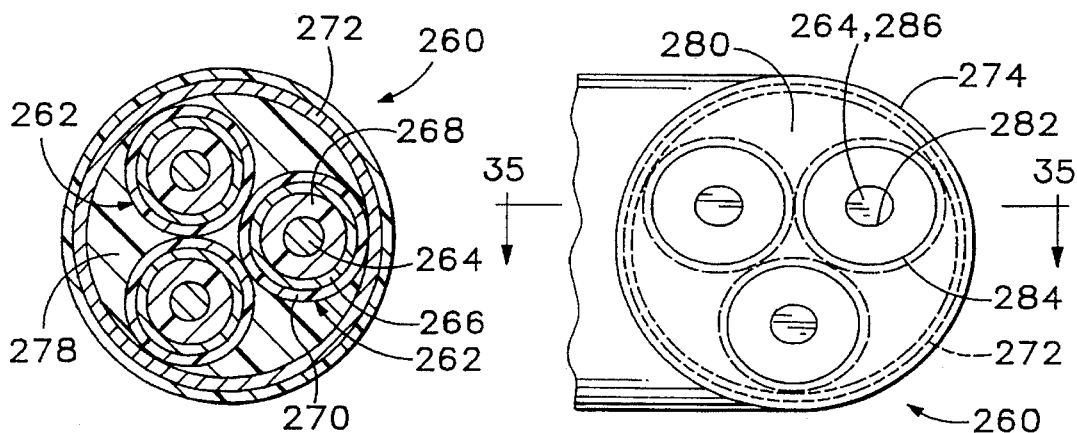
FIG. 33 is a sectional view, at an enlarged scale, taken along line 33—33 of FIG. 32.
FIG. 34 is a view taken along line 34—34 of FIG. 32, at an enlarged scale, showing the active electrode sites of the microelectrode.
Figure 35:
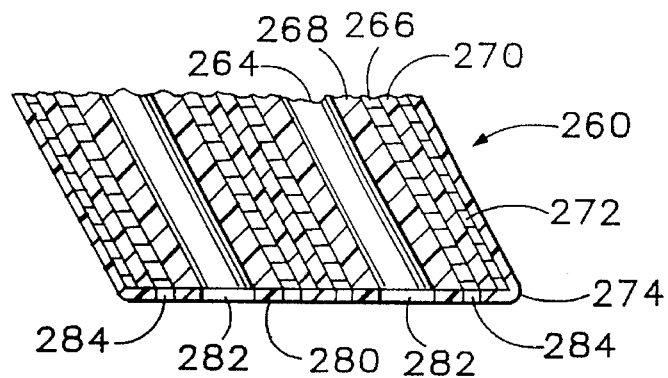
FIG. 35 is a sectional view taken along line 35—35 of FIG. 34.

Yet a further embodiment of the invention is a biologically implantable multiconductor microelectrode 230, shown in FIGS. 28–31, in which mechanical support for the electrical conductors extending as continuations of a multiconductor is provided by a thin-walled tubular metal needle 234. The distal end 236 of the needle is cut at a bevel angle 238, preferably 65° or greater. Several fine wires 240, each covered by a tightly adhered thin coating 242 of a biologically compatible dielectric material such as one of those mentioned previously herein, extend through the tubular needle 234 to the distal end and are held in place within the lumen of the tubular needle by being potted in dielectric material 244. A potting material suitable for securing the coaxial conductor pairs within the hollow needle is available under the trade name EPO TEK 301 from Epoxy Technologies, Inc. of Billerica, Mass. Preferably each of the fine wires 240 is bent toward the plane 246 defined by the beveled surface of the distal end 236 of the needle, to establish the location of the end of the wire 240 where desired and to present a small active electrode site surface area when the fine wires are cut to expose them as shown in FIG. 30.

Depending upon the spacing required and the impedance required of the active electrode site, an additional coating 248 of dielectric material may be applied over the beveled surface after it has been cut and polished. A UV laser beam may then be used as previously described herein to form openings 250 through the layer of dielectric material and expose a clean contact surface area for each active electrode site 252 on the microelectrode, in order to control more precisely the location and size of each active electrode site 252 defined.

In a biologically implantable multiconductor microelectrode 260 which is a slightly different embodiment of the invention, shown in FIGS. 32–35, a small number of coaxial conductor pairs 262, each including a center conductor 264, a shield conductor 266 which may be of a served wire or foil, a quantity of dielectric material 268 between the center conductor 264 and the shield 266, and an outer jacket 270 of dielectric material, extend through the lumen of a tubular needle 272 having a beveled distal end 274 which may be cut at a shallow angle 276 of, for example, 30°. The coaxial conductor pairs 262 are held fixedly located within the lumen of the tubular needle 272 by potting material 278 such as that previously described, and are cut flush with the beveled surface at the distal end 274 of the needle 272.

The beveled surface may then be covered by a final coating 280 of dielectric material, after which openings 282 are prepared by use of a UV laser beam controlled as previously described to provide a clean contact surface area 286 of a desired size in each of the desired active electrode sites to connect with the center conductor 264 of each coaxial pair. Similarly, the UV laser is used to create a circular groove 284 through the coating 280 to expose the shield conductor 266 of each coaxial pair 262, thus providing bipolar active electrode sites each having a desired electrical field characteristic made possible by the coaxial conductor pairs. Thereafter, both the center conductor 264 and shield conductor 266 of the coaxial pairs 262 may, if desired, be built up by deposits of metal to provide the actual contact surfaces of each active electrode site. It will be understood that at the proximal end of the tubular needle the coaxial conductor pairs may be held together as a flexible cable 286 of conductors extending to a suitable connector (not shown).

Figure 36:
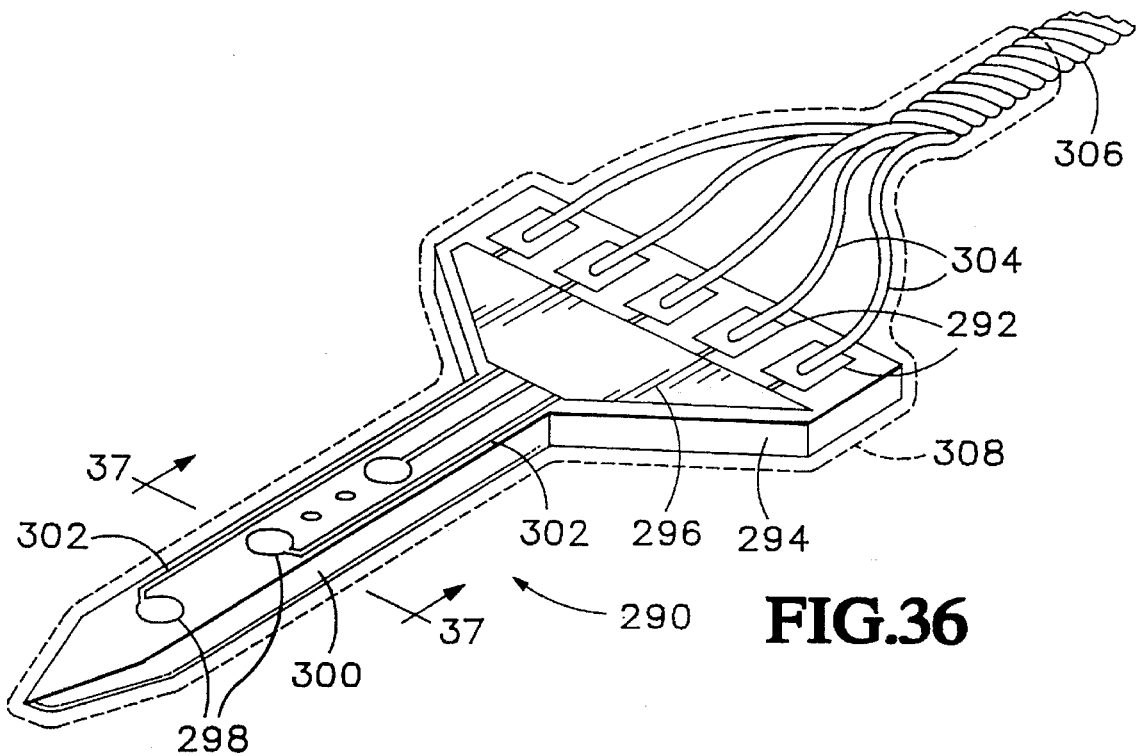
FIG. 36 is a view of a biologically implantable multiconductor microelectrode incorporating a microscopic integrated circuit, together with a part of a multiconductor cable, prepared in accordance with the present invention.
Figure 37:
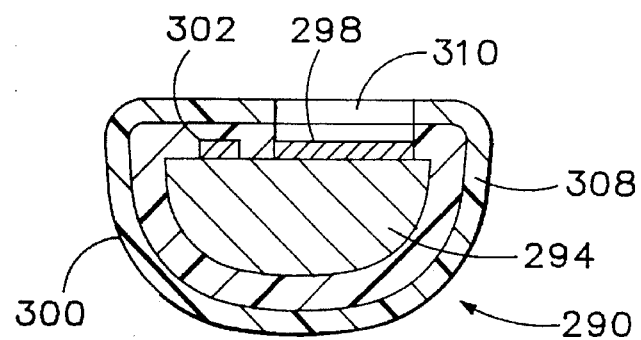
FIG. 37 is a sectional view, taken along line 37—37, of the microelectrode shown in FIG. 36.

As shown in FIGS. 36 and 37, a biologically implantable multiconductor microelectrode 290 is a tiny integrated circuit chip produced by solid state semiconductor production techniques to define several terminal pads 192 on a substrate wafer 294. An integrated circuit 296, not shown in detail, is connected to the terminal pads 292. Several active electrode sites 298 are located on a long narrow probe tip 300 small enough to be placed in a nerve, and interconnect lines 302 extend from the integrated circuit to the electrode sites 298.

Extremely fine individually insulated wires 304 are connected to the terminal pads 292 and are stranded to form a cable 306 leading away from the microelectrode 290 and may be held together by an outer coating of dielectric material (not shown). An overall coating 308, several microns thick, of a biologically compatible and implantable dielectric material, such one of those described previously herein, covers the entire microelectrode 290 and the interconnection to it of the several wires 304, to protect the microelectrode 290 and the cable 306 as an integral assembly once it has been implanted.

In order to communicate by electrical impulses between the microelectrode 290 and a nerve, each of the active electrode sites 298 is exposed through an opening 310 prepared in accordance with the method of the invention by ablating the overlying dielectric material through the use of intense ultraviolet light as from a UV laser in the manner previously described. This produces precisely located electrode sites 298 of precise size on which additional metal may be deposited if desired to raise the electrode site flush with or protruding above the coating 308. The dielectric material of the coating 308 is tightly adhered to the probe tip 300, including a layer of dielectric material 312, if any, surrounding the electrode site 298, as a result of brief thermal fusing and resolidification of a surface layer of the coating 308, as described previously with respect to the microelectrode 40.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A biologically implantable multiconductor microelectrode, comprising:
    (a) a plurality of fine wires, all of said fine wires being wrapped helically around a sharp-pointed electrode support core;
    (b) a quantity of a dielectric material covering a portion of each of said plurality of fine wires and electrically insulating said fine wires from each other and holding said fine wires together in a predetermined spatial relationship with each other, said quantity of dielectric material having an outer surface and defining a plurality of openings, each of said openings communicating between said outer surface and a respective one of said fine wires and exposing a predetermined area of a respective one of said fine wires therethrough.

2. The biologically implantable multiconductor microelectrode of claim 1 wherein said sharp-pointed core is of metal and wherein said core and said fine wires are held together as an integral structure by said dielectric material, said dielectric material insulating said core from each of said fine wires, said microelectrode including a respective active electrode site defined by each of said openings through said dielectric material.

3. A biologically implantable multi-conductor microelectrode, comprising:
    (a) a plurality of fine wires each having a surface, said fine wires of said plurality being arranged in a planar array; and
    (b) a thin coating of a dielectric material having a predetermined thickness covering a portion of each of said plurality of fine wires, electrically insulating said fine wires from each other and holding said fine wires together in a predetermined spatial relationship with each other, said coating of dielectric material having an outer surface and defining a plurality of openings, said openings being defined in said dielectric material within said planar array and each of said openings extending inward from said outer surface and communicating between said outer surface and a predetermined area on a surface of a respective one of said fine wires at a location spaced inwardly from said outer surface.

4. The biologically implantable multi-conductor microelectrode of claim 3, including a respective deposit of electrically conductive material different from said fine wires located within each of said openings and electrically connected with said predetermined area on said surface of the respective one of said fine wires within said opening.

5. A biologically implantable multi-conductor microelectrode, comprising:
    (a) an integrated circuit substrate including a portion defining a probe tip;
    (b) a plurality of active electrode sites each including exposed conductive material located on said probe tip;
    (c) a respective electrical interconnect line, located on said substrate and electrically interconnected with each said active electrode site located on said probe tip, and extending away from said active electrode site along said probe tip;
    (d) a plurality of terminal pads located on said substrate and spaced apart from said probe tip;
    (e) a plurality of conductors each connected electrically to a respective one of said terminal pads; and
    (f) a substantially continuous coating of a dielectric material covering said interconnect line, said terminal pads, respective portions of said conductors connected to said terminal pads, and said substrate, a plurality of openings being defined through said coating, and each said opening exposing a predetermined area of said conductive material located on said probe tip and thereby defining a respective one of said active electrode sites, said coating of dielectric material being tightly adhered to said probe tip immediately adjacent and surrounding each of said active electrode sites.

6. In combination, a miniature electrical conductor cable and a biologically implantable microelectrode, comprising:
    (a) a pair of opposite ends and an intermediate portion of said cable;
    (b) a plurality of very small elongate flexible electrical conductors each having respective opposite ends corresponding with said opposite ends of said cable, each said conductor having a respective intermediate portion extending between said opposite ends thereof, said intermediate portions of said conductors being located closely alongside one another in a predetermined arrangement defining said intermediate portion of said cable;
    (c) a first layer of a first electrical insulating material constituting a separate thin substantially continuous coating on each of said plurality of conductors;
    (d) at least one of said opposite ends of said cable having a respective ribbonized portion including a respective transition portion in which said plurality of conductors diverge from one another and a terminal portion in which said plurality of conductors are arranged generally parallel with each other and are separated from one another by a predetermined pitch; and
    (e) said plurality of conductors in said transition portions and terminal portions of said ribbonized portion included in said one of said opposite ends being covered and surrounded by and supported by a quantity of a ribbonizing material and being held in predetermined relative positions with respect to each other by said ribbonizing material, a plurality of openings being defined through said ribbonizing material and said first layer in said terminal portion, and a predetermined area of each of said conductors being cleanly exposed adjacent said ribbonizing material within each said opening as a respective active electrode site, said active electrode sites together constituting a microelectrode.

7. The combination of claim 6, each of said plurality of flexible electrical conductors including a second layer of a second insulating material constituting a separate thin coating over said first layer of said first electrical insulating material, said plurality of openings extending through said second layer.

8. The combination of claim 7 wherein said second insulating material is biologically compatible with implantation in a living body.

9. The combination of claim 7, including a third layer of a third insulating material, in the form of an overcoating over said second layer of insulating material on each of said plurality of conductors, said third layer of said third insulating material interconnecting adjacent ones of said plurality of elongate conductors, holding all of said elongate conductors closely alongside one another in a predetermined arrangement throughout said intermediate portion of said cable.

10. The combination of claim 9 wherein said third insulating material is biologically compatible with implantation in a living body.

11. The combination of claim 6, including at least a respective outermost layer of insulating material which is biologically compatible with being implanted in a living body, surrounding each of said plurality of conductors.

12. The combination of claim 6, including an outer layer of dielectric material in said intermediate portion of said cable, holding said intermediate portions of each of said conductors parallel with each other in a ribbon-like arrangement in said intermediate portion of said cable.

13. The combination of claim 6 wherein all of said plurality of conductors are arranged in a circular stranded arrangement in said intermediate portion of said cable.

14. The combination of claim 13 including an outer layer of insulating material in said intermediate portion of said cable coating the outside of at least some of said plurality of conductors over said first layer and any additional separate layers of insulating material covering said first layer on any of said plurality of conductors, with said outer layer mechanically interconnecting adjacent ones of said plurality of conductors in said intermediate portion of said cable.

15. A biologically implantable multiconductor microelectrode, comprising:
   (a) a plurality of fine wires each having a surface;
   (b) a quantity of a dielectric material, including a thin coating having a predetermined thickness, covering a portion of said surface of each of said plurality of fine wires and electrically insulating said fine wires from each other and holding said fine wires together in a predetermined spatial relationship with each other, said fine wires being separated from one another by a distance established by said predetermined thickness of said coating, said quantity of dielectric material having an outer surface and defining a plurality of openings, each of said openings extending inward from said outer surface and communicating between said outer surface and a predetermined area on said surface of a respective one of said fine wires at a location spaced inwardly from said outer surface.

16. The biologically implantable multiconductor microelectrode of claim 15 including a respective deposit of conductive metal different from said fine wires located in each of said plurality of openings in said electric material, each of said deposits of conductive metal being mechanically and electrically interconnected with the respective one of said fine wires in the respective opening.

17. The biologically implantable multiconductor microelectrode of claim 16 wherein each of said plurality of openings defines a space and each said deposit of electrically conductive material fills the space respectively defined by one of said openings.

18. The biologically implantable multiconductor microelectrode of claim 17 wherein each said deposit of electrically conductive material includes a terminal contact surface located flush with an outer surface of said dielectric material surrounding the respective opening in which said electrically conductive material is located.

19. A miniature electrical conductor cable suitable for implantation in a living body, comprising:
   (a) a pair of opposite ends and an intermediate portion;
   (b) a plurality of very small elongate flexible electrical conductors each having respective opposite ends corresponding with said opposite ends of said cable, each said conductor having a respective intermediate portion extending between said opposite ends thereof, said intermediate portions of said conductors being arranged together with each other in a helical circular strand defining said intermediate portion of said cable;
   (c) a respective first layer of a first electrical insulating material, said first layer having a thickness and constituting a separate thin substantially continuous coating, surrounding said intermediate portion of each of said plurality of conductors;
   (d) at least one of said opposite ends of said cable having a respective ribbonized portion defined by said plurality of conductors of said cables being substantially covered by and supported by a quantity of a ribbonizing material adhered thereto and having a predetermined thickness greater than that of said first layer, said conductors being held in predetermined relative positions with respect to each other by said ribbonizing material, said ribbonized portion including a respective transition portion adjacent said intermediate portion and said plurality of conductors diverging from one another in a single stratum in said transition portion, and said ribbonized portion also including a respective terminal portion adjacent said transition portion, said plurality of conductors in said terminal portion being parallel with each other and separated from one another by a predetermined pitch; and
   (e) an electrically connectable surface portion of each of said conductors being exposed adjacent said ribbonizing material of said terminal portion.

20. The miniature electrical conductor cable of claim 19, each of said plurality of flexible electrical conductors having associated therewith throughout all of said intermediate portion a respective second layer of a second insulating material constituting a separate thin coating over said first layer of said first electrical insulating material.

21. The miniature electrical conductor cable of claim 20 wherein said second insulating material is biologically compatible with implantation in a living body.

22. The miniature electrical conductor cable of claim 21 wherein said second insulating material is a polyesterimide material.

23. The miniature electrical conductor cable of claim 20 wherein said second insulating material has a lower melting temperature than said first insulating material.

24. The miniature electrical conductor cable of claim 20, including a third layer of a third insulating material, in the form of an overcoating over said second layer of insulating material on each of said plurality of conductors, said third layer of said third insulating material interconnecting adjacent ones of said plurality of elongate conductors, holding all of said elongate conductors closely alongside one another in a predetermined arrangement throughout said intermediate portion of said cable.

25. The miniature electrical conductor cable of claim 24 wherein said third insulating material is biologically compatible with implantation in a living body.

26. The miniature electrical conductor cable of claim 25 wherein said third insulating material is a polyesterimide material.

27. The miniature electrical conductor cable of claim 25 wherein said third insulating material is a polyurethane material.

28. The miniature electrical conductor cable of claim 25 wherein said third insulating material is a silicone material.

29. The cable of claim 19 wherein said ribbonized portion includes a portion of each of said conductors substantially free from any of said first layer of said first electrical insulating material.

30. The cable of claim 19 wherein each of said conductors has associated therewith a surrounding outermost layer of an insulating material that is biologically compatible with being implanted within a living body.

31. The cable of claim 19 wherein said thickness of said first layer, measured in a radial direction respectively from a surface of each of said plurality of conductors, is no greater than about 7 microns.

32. The cable of claim 31 wherein said thickness of said first layer is in the range of 3–6 microns.

33. The cable of claim 19 including an outer layer of insulating material coating respective portions of at least some of said conductors, exterior of said first layer and thereby holding together all of said plurality of conductors in said circular stranded arrangement in said intermediate portion of said cable.

34. The miniature electrical conductor cable of claim 19 wherein said first electrical insulating material is a polyimide resin material.

35. The miniature electrical conductor cable of claim 19 wherein said first electrical insulating material is a polyurethane material.

36. The miniature electrical conductor cable of claim 19 wherein said first electrical insulating material is a silicone material.

37. The miniature electrical conductor cable of claim 19 wherein said first electrical insulating material is a polymeric fluorocarbon material.

38. The miniature electrical conductor cable of claim 19 wherein each of said elongate electrical conductors is a single wire no larger than about 0.040 mm in diameter.

39. The miniature electrical conductor cable of claim 19 wherein said intermediate portion of said cable includes a centrally located tube defining a lumen within said helical circular strand of conductors.

\* \* \* \* \*